United States Patent [19]

Valet et al.

[11] Patent Number: 5,756,793

[45] Date of Patent: May 26, 1998

[54] PROTECTIVE COATING FOR WOOD

[75] Inventors: Andreas Valet, Binzen, Germany; Roger Meuwly, Cournillens, Switzerland

[73] Assignee: Ciba-Specialty Chemicals Corporation, Tarrytown, N.Y.

[21] Appl. No.: 799,177

[22] Filed: Feb. 12, 1997

Related U.S. Application Data

[62] Division of Ser. No. 384,188, Feb. 6, 1995.

[30] Foreign Application Priority Data

Feb. 10, 1994 [CH] Switzerland ............... 405/94

[51] Int. Cl.$^6$ .................. C07F 7/08; C07F 7/18
[52] U.S. Cl. ............. 556/436; 106/287.13; 106/287.14; 106/287.16; 106/287.35; 568/332; 568/333
[58] Field of Search ............ 106/287.13, 287.14, 106/287.16, 287.35; 556/436; 568/332, 333

[56] References Cited

FOREIGN PATENT DOCUMENTS 810570   3/1959   United Kingdom ............ 568/332

OTHER PUBLICATIONS

Pat. Abst. of JP vol. 17 No. 41 (M–1359).

Derwent Abstr. 85–052258 [09].

Primary Examiner—Paul F. Shaver
Attorney, Agent, or Firm—Victoria M. Malia; David R. Crichton

[57] ABSTRACT

The invention relates to a method of protecting surfaces of wood against damage by light by treatment with a coating composition comprising a benzophenone of the formula I

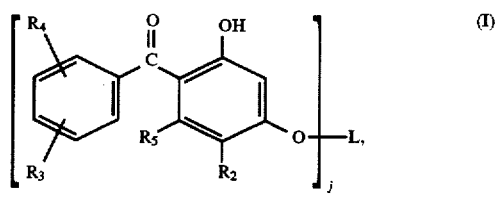

in which the substituents are defined as in claim 1.

6 Claims, No Drawings

PROTECTIVE COATING FOR WOOD

This is a DIVISIONAL of application Ser. No. 08/384,188 filed Feb. 6, 1995.

The invention relates to a method of protecting surfaces of wood against damage by light and to a protective coating for wood.

Surfaces of wood which are exposed to intense sunlight are damaged primarily by the UV component of sunlight. The polymeric constituents of the wood are degraded, leading to a roughening and discoloration of the surface. Subsequently, further damage results from infestation by microorganisms, especially by fungi.

The usual method of protecting wood against damage by light without giving up the visual image of the wood surface is to coat it with a colourless varnish containing a light stabilizer, in particular a UV absorber.

It has now been found that selected UV absorbers from the benzophenone series display a distinct stabilizer action against the effect of light, when applied in a coating composition.

The invention thus relates to a method of protecting surfaces of wood against damage by light, by treatment with a coating composition comprising a benzophenone of the formula

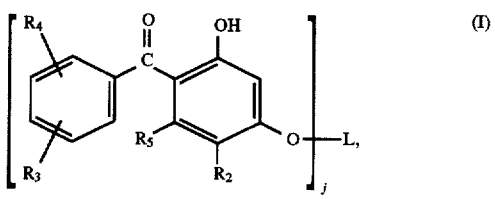

in which
i is a number from one to four;
L if i is one is H, $C_1$-$C_{20}$alkyl, $C_2$-$C_{20}$alkyl which is substituted by one or two —OH, by carboxyl, by $C_1$-$C_{12}$alkoxy, by phenoxy, by $C_2$-$C_{20}$alkylcarbonyl, by $C_3$-$C_{20}$alkenylcarbonyl, by $C_2$-$C_{20}$alkanoyloxy, by $C_3$-$C_{20}$alkenoyloxy or by phenyl, glycidyl, $C_4$-$C_{20}$alkyl which is interrupted by one to six O atoms or by one or two carbonyloxy or oxycarbonyl groups, $C_2$-$C_{18}$alkenyl, $C_2$-$C_{18}$alkanoyl, $C_3$-$C_{18}$alkenoyl, benzoyl, benzoyl which is substituted by one or two $C_1$-$C_4$alkyl groups, substituted or unsubstituted phenyl or naphthyl, or a group of the formula II, III, IV, V or VI:

—(CH$_2$)$_j$—CH(OH)—(CH$_2$)$_k$—O—R$_9$ (II) where j, k=0–4;

—(CH$_2$)$_m$—COOR$_9$ (III) where m=1–4;
in which R$_9$ is $C_1$-$C_{18}$alkyl or phenyl;

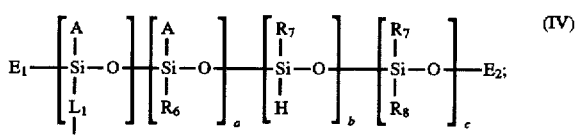

in which
a=0–50, b=0–50 and c=0–50;
A is R$_7$ or —O—Si(R$_7$)$_3$;
E$_1$ is OH, $C_1$-$C_{12}$alkyl, $C_1$-$C_4$alkoxy, cyclohexyl, phenyl or —O—Si(R$_7$)$_3$;
E$_2$ is H, $C_1$-$C_{12}$alkyl, cyclohexyl, phenyl, -Si(R$_7$)$_3$ or —Si(R$_6$)(R$_7$)$_2$;
in which E$_1$ and E$_2$ together may also be a direct bond;

L$_1$ is a direct bond or a divalent group of the formula
—C$_n$H$_{2n}$—, —(CH$_2$)$_n$—O—,
—CH$_2$CH(OH)CH$_2$—O— or —CH$_2$CH(OH)CH$_2$—O—(CH$_2$)$_3$—, where n=1–4;
R$_6$ is a radical of the formula

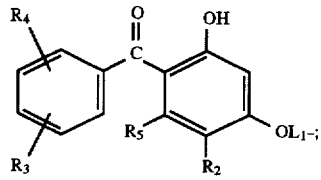

R$_7$ is $C_1$-$C_{12}$alkyl, $C_1$-$C_4$alkoxy, cyclohexyl or phenyl; and R$_8$ is $C_1$-$C_{18}$alkyl, $C_1$-$C_4$alkoxy, $C_5$-$C_7$cycloalkyl or phenyl;

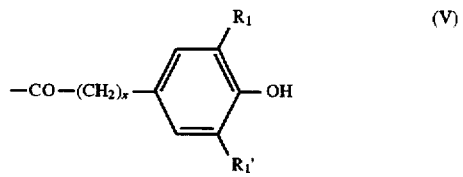

in which x is 0, 1 or 2;
R$_1$ is $C_1$-$C_{12}$alkyl or $C_5$-$C_8$cycloalkyl; and
R' is secondary or tertiary $C_3$-$C_{12}$alkyl or $C_5$-$C_8$cycloalkyl;

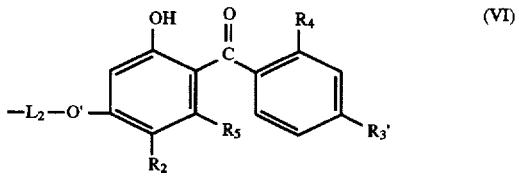

in which L$_2$ is as defined for L if i is two; and R$_3$' is H or $C_1$-$C_{18}$alkyl;
L if i is two is $C_1$-$C_{12}$alkylene, $C_3$-$Cl_2$alkylene which is substituted by —OH, by $C_1$-$C_8$alkoxy, by $C_2$-$C_{20}$alkoxycarbonyl, by $C_2$-$C_{20}$alkanoyloxy, by $C_3$-$C_{20}$alkenoyloxy or by a silyl group of the formula (IV), $C_4$-$C_{20}$alkylene which is interrupted by one to six O atoms or by one or two carbonyloxy or oxycarbonyl groups, o-xylylene, m-xylylene, p-xylylene, isophthaloyl, phthaloyl, terephthaloyl or α,ω-$C_4$-$C_{12}$alkanedioyl;
L if i is three is $C_3$-$C_{12}$alkanetriyl, $C_3$-$C_{12}$alkanetrioyl, trimellitoyl or $C_6$-$C_{20}$alkanetriyl which is interrupted by three carbonyloxy or oxycarbonyl groups;
L if i is four is $C_4$-$C_{16}$alkanetetrayl, $C_4$-$C_{16}$alkanetetrayl, pyromellitoyl or $C_8$-$C_{24}$alkanetetrayl which is interrupted by four carbonyloxy or oxycarbonyl groups;
R$_2$ is H, $C_1$-$C_{18}$alkyl or Cl;
R$_3$ is H, Cl, —OCH$_3$, —SR$_{10}$, —SOR$_{10}$ or —SO$_2$R$_{10}$;
R$_4$ is H, —OH, $C_1$-$C_{18}$alkyl or $C_2$-$C_{18}$alkenyl;
R$_5$ is H, —OL, where L is as defined for if i is one, or Cl; and
R$_{10}$ is $C_1$-$C_{20}$alkyl, $C_2$-$C_{20}$alkyl which is substituted by —OH, by $C_1$-$C_{12}$alkoxy, by a silyl group of the formula (IV), by $C_2$-$C_{12}$alkanoyloxy, by $C_3$-$C_{12}$alkenoyloxy or by halogen, $C_3$-$C_{18}$alkenyl, $C_5$-$C_{12}$cycloalkyl, $C_7$-$C_{15}$phenylalkyl, $C_6$-$C_{10}$aryl, $C_6$-$C_{10}$aryl which is substituted by one or two $C_1$-$C_4$alkyl groups, or 1,1,2,2-tetrahydroperfluoro-$C_6$-$C_{16}$alkyl;
under the condition that, if i is one, at least one of the radicals R$_2$, R$_3$ and R$_5$ is other than H and R$_3$ is not —OCH$_3$, if R$_2$ and R$_5$ are H and L is methyl.

Suitable alkyl substituents having up to 20 carbon atoms are the radicals such as methyl, ethyl, propyl, butyl, pentyl, hexyl, octyl, decyl, dodecyl, tetradecyl, hexadecyl, octadecyl and eicosyl, and corresponding branched isomers.

Suitable alkenyl substituents having up to 18 carbon atoms are the radicals such as 1-propenyl, allyl, methallyl, 2-butenyl, 2-pentenyl, 2-hexenyl, 2-octenyl, 4-tert-butyl-2-butenyl or radicals derived from the above alkyl radicals.

Suitable alkoxy substituents having up to 12 carbon atoms are the radicals such as methoxy, ethoxy, propoxy or butoxy and corresponding branched isomers or radicals derived from the above alkyl radicals.

Suitable alkanoyl substituents are the radicals such as acetyl, propionyl, butyryl, capryl or lauroyl and corresponding branched isomers or radicals derived from the above alkyl radicals.

Suitable alkanetriyl substituents are the radicals such as 1,2,3-propanetriyl, 1,2,2-neopentanetriyl or 1,2,2-neohexanetriyl and corresponding branched isomers or radicals derived from the above alkyl radicals.

Suitable alkanetetrayl substituents are the radicals such as pentaerythrityl or 1,2,3,4-butanetetrayl and corresponding branched isomers or radicals derived from the above alkyl radicals.

Suitable cycloalkyl substituents are the radicals such as cyclopentyl, cyclohexyl, cycloheptyl, cyclooctyl or cyclododecyl.

Suitable phenylalkyl substituents are the radicals such as benzyl, phenethyl, α-methylbenzyl or α,α-dimethylbenzyl.

Suitable aryl substituents are the radicals such as phenyl or naphthyl.

Suitable alkylene substituents are the radicals such as ethylene, tetramethylene, hexamethylene, 2-methyl-1,4-tetramethylene, 2,2-dimethyl-1,3-trimethylene, octamethylene, decamethylene or dodecamethylene.

Suitable substituted or unsubstituted phenyl or naphthyl substituents are the radicals such as phenyl, benzyl, cumyl, α- or β-naphthyl. In addition to $C_1$-$C_4$alkyl radicals the phenyl or naphthyl radicals may also be substituted by halogen, especially Cl or Br, and by $C_1$-$C_4$alkoxy.

Suitable halogen substituents are F, Br and, with particular preference, Cl.

Compounds which contain a radical of formula IV may have a linear or a cyclic structure. The individual monomer units of the radical of the formula IV are distributed randomly.

Preferred compounds of the formula (I) are those in which at least one of the radicals $R_2$, $R_3$ and $R_5$ is other than H.

Additional preferred compounds of the formula (I) are those in which the radical $R_3$ is in the para position to the CO radical and/or the radical $R_4$ is in the ortho position to the CO radical.

Still further preferred compounds of the formula (I) are those in which i is one or two, with particular preference one.

Further preferred compounds of the formula (I) are those in which L if i is one is H, $C_1$-$C_{20}$alkyl, $C_2$-$C_{20}$alkyl which is substituted by one or two —OH, by $C_1$-$C_{12}$alkoxy, by phenoxy, by $C_2$-$C_{20}$alkylcarbonyl or by phenyl, glycidyl, $C_4$-$C_{20}$alkyl which is interrupted by one to six O atoms, $C_2$-$C_{18}$alkenyl, unsubstituted or substituted phenyl or naphthyl, or a group of the formula II, III or IV:

—$(CH_2)_j$—CH(OH)—$(CH_2)_k$—O—$R_9$ (II) where j, k=0–4;
—$(CH_2)_m$—COOR$_9$ (III) where m=1–4;
in which $R_9$ is $C_1$-$C_{18}$alkyl or phenyl;

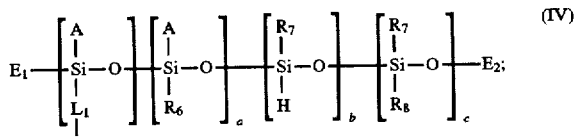

in which
a=0–50, b=0–50 and c=0–50;
A is $R_7$ or —O—Si($R_7$)$_3$;
$E_1$ is OH, $C_1$-$C_{12}$alkyl, $C_1$-$C_4$alkoxy, cyclohexyl, phenyl or —O—Si($R_7$)$_3$;
$E_2$ is H, $C_1$-$C_{12}$alkyl, cyclohexyl, phenyl, —Si($R_7$)$_3$ or —Si($R_6$)($R_7$)$_2$;
in which $E_1$ and $E_2$ together may also be a direct bond;
$L_1$ is a direct bond or a divalent group of the formula —$C_nH_{2n}$—, —$(CH_2)_n$—O—, —$CH_2CH(OH)CH_2$—O— or —$CH_2CH(OH)CH_2$—O—$(CH_2)_3$—, where n=1–4;
$R_6$ is a radical of the formula

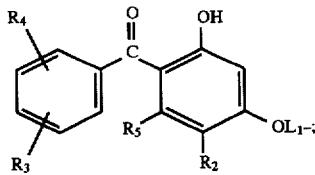

$R_7$ is $C_1$-$C_{12}$alkyl, $C_1$-$C_4$alkoxy, cyclohexyl or phenyl; and
$R_8$ is $C_1$-$C_{18}$alkyl, $C_1$-$C_4$alkoxy, $C_5$-$C_7$cycloalkyl or phenyl.

Additional preferred compounds of the formula (I) are those in which $R_3$ is H, Cl, —OCH$_3$, —SR$_{10}$ or —SO$_2$R$_{10}$.

Further preferred compounds of the formula (I) are those in which $R_{10}$ is $C_1$-$C_{20}$alkyl, $C_2$-$C_{20}$alkyl which is substituted by —OH or by $C_1$-$C_{12}$alkoxy, $C_3$-$C_{18}$alkenyl, $C_5$-$C_{12}$cycloalkyl, $C_7$-$C_{15}$phenylalkyl, $C_6$-$C_{10}$aryl or $C_6$-$C_{10}$aryl which is substituted by one or two $C_1$-$C_4$alkyl groups.

Particularly preferred compounds of the formula (I) are those in which i is one;
L is H, $C_1$-$C_{12}$alkyl, $C_2$-$C_{12}$alkenyl, phenyl, naphthyl or a radical of the formula II, III or IV:
—$(CH_2)_j$—CH(OH)—$(CH_2)_k$—O—$R_9$ (II) where j, k=0–4;
—$(CH_2)_m$—COOR$_9$ (III) where m=1–4;
in which $R_9$ is $C_1$-$C_{18}$alkyl or phenyl;

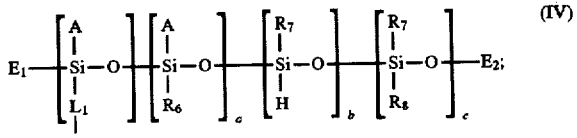

in which
a=0–50, b=0 and c=0–50;
A is $R_7$ or —O—Si($R_7$)$_3$;
$E_1$ is OH, $C_1$-$C_{12}$alkyl, $C_1$-$C_4$alkoxy, cyclohexyl, phenyl or —O—Si($R_7$)$_3$;
$E_2$ is H, $C_1$-$C_{12}$alkyl, cyclohexyl, phenyl, —SiR$_6$($R_7$)$_2$ or —Si($R_7$)$_3$;

in which $E_1$ and $E_2$ together may also be a direct bond;

$L_1$ is a direct bond or a divalent group of the formulae $-C_nH_{2n}-$, $-(CH_2)_n-O-$ or $-CH_2CH(OH)CH_2-O-(CH_2)_3-$, where n=1–4;

$R_6$ is a radical of the formula

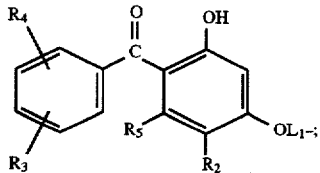

$R_7$ is $C_1$-$C_{12}$alkyl, $C_1$-$C_4$alkoxy, cyclohexyl or phenyl; and $R_8$ is $C_1$-$C_{18}$alkyl, $C_1$-$C_4$alkoxy, $C_5$-$C_7$cycloalkyl or phenyl;

$R_2$ is $C_1$-$C_{12}$alkyl or Cl or, if $R_5$ is —OL or Cl or $R_3$ is —$SR_{10}$ or —$SO_2R_{10}$, is also H;

$R_3$ is Cl, —$OCH_3$, —$SR_{10}$, —$SO_2R_{10}$ or, if $R_2$ or $R_5$ is other than H, is also H;

$R_4$ is H, $C_1$-$C_{12}$alkyl or $C_2$-$C_{12}$alkenyl;

$R_5$ is H, —OL or Cl; and $R_{10}$ is $C_1$-$C_{20}$alkyl, $C_2$-$C_{20}$alkyl which is substituted by —OH or by $C_1$-$C_{12}$alkoxy, $C_3$-$C_{18}$alkenyl, $C_5$-$C_{12}$cycloalkyl, $C_7$-$C_{15}$phenylalkyl, $C_6$-$C_{10}$aryl or $C_6$-$C_{10}$aryl which is substituted by one or two $C_1$-$C_4$alkyl groups.

Further particularly preferred compounds of the formula (I) are those in which i is one;

L is H, $C_1$-$C_{12}$alkyl, $C_2$-$C_{12}$alkenyl, phenyl, naphthyl or a radical of the formula II, III or IV $-(CH_2)_j-CH(OH)-(CH_2)_k-O-R_9$ (II) where j, k=0–4;

$-(CH_2)_m-COOR_9$ (III) where m=1–4;

in which $R_9$ is $C_1$-$C_{18}$alkyl or phenyl;

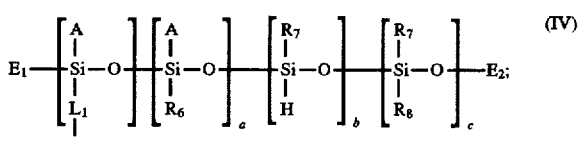

in which a=0–50, b=0–50 and c=0–50;

A is $R_7$ or —O—Si($R_7$)$_3$;

$E_1$ is OH, $C_1$-$C_{12}$alkyl, $C_1$-$C_4$alkoxy, cyclohexyl, phenyl or —O—Si($R_7$)$_3$;

$E_2$ is H, $C_1$-$C_{12}$alkyl, cyclohexyl, phenyl, —$SiR_6$($R_7$)$_2$ or —Si($R_7$)$_3$;

in which $E_1$ and $E_2$ together may also be a direct bond;

$L_1$ is a direct bond or a divalent group of the formula $-C_nH_{2n}-$, $-(CH_2)_n-O-$ or $-CH_2CH(OH)CH_2-O-(CH_2)_3-$, where n=1–4;

$R_6$ is a radical of the formula

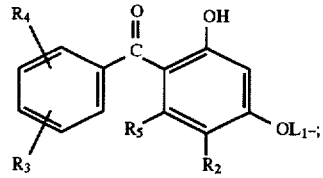

$R_7$ is $C_1$-$C_{12}$alkyl, $C_1$-$C_4$alkoxy, cyclohexyl or phenyl; and $R_8$ is $C_1$-$C_{18}$alkyl, $C_1$-$C_4$alkoxy, $C_5$-$C_7$cycloalkyl or phenyl;

$R_2$ is $C_1$-$C_{12}$alkyl or Cl or, if $R_5$ is —OL or Cl, is also H;

$R_3$ is Cl, —$OCH_3$ or, if $R_2$ or $R_5$ is other than H, is also H;

$R_4$ is H, $C_1$-$C_{12}$alkyl or $C_2$-$C_{12}$alkenyl; and $R_5$ is H, —OL or Cl.

Very particularly preferred compounds of the formula (I) are those in which

A)

i is one;

L is —$CH_2$-CH(OH)—$CH_2$—O—$R_9$ (II);

$R_2$ is $C_1$-$C_{12}$alkyl;

$R_3$, $R_4$ and $R_5$ are H; and $R_9$ is $C_1$-$C_{18}$alkyl; or

B)

i is one;

L is $C_1$-$C_{12}$alkyl;

$R_2$ is $C_1$-$C_{12}$alkyl; and $R_3$, $R_4$ and $R_5$ are H; or

C)

i is one;

L is $C_1$-$C_{12}$alkyl;

$R_2$ is $C_1$-$C_{12}$alkyl;

$R_3$ is Cl; and $R_4$ and $R_5$ are H; or

D)

i is one;

L is —$(CH)_m$—$COOR_9$ (III) where m=1–4;

$R_2$ is $C_1$-$C_{12}$alkyl;

$R_3$, $R_4$ and $R_5$ are H; and $R_9$ is $C_1$-$C_{18}$alkyl; or

E)

i is one;

L is $C_1$-$C_{12}$alkyl;

$R_2$, $R_4$ and $R_5$ are H;

$R_3$ is —$SR_{10}$ or —$SO_2R_{10}$; and $R_{10}$ is $C_1$-$C_{12}$alkyl or phenyl.

In certain cases it may be of advantage to use two or more of the abovementioned benzophenones. Particular preference is given to mixtures comprising a benzophenone of the formula (I) in which $R_2$ and $R_3$ and $R_5$ are hydrogen with a benzophenone of the formula (I) in which at least one of the radicals $R_2$, $R_3$ and $R_5$ is not hydrogen. The ratio by weight of the benzophenones in the mixture is conventionally from 5:1 to 1:5, with ratios of from 3:1 to 1:3 being preferred.

In the method according to the invention, the coating compositions may contain the components described in more detail below. The invention also relates to protective coating compositions for wood, comprising a compound of the formula (I). One possible division of the protective coatings for wood is the differentiation between primer or impregnating coat and topcoat, as explained below. Preference is given to a topcoat composition and to the method which uses a topcoat composition containing a compound of the formula I. The preferences indicated above for the compounds of the formula I in the method according to the invention apply equally to the protective coating compositions.

When a primer or impregnating coat is constructed, it is intended to penetrate the surface of the wood and therefore to be of relatively low viscosity. Examples of solvents which can be used for this purpose are aliphatic hydrocarbons such as, for example, certain petroleum fractions. Further examples of solvents are aromatic hydrocarbons such as, for example, toluene or xylene; alcohols such as, for example, methanol, ethanol, isopropanol or butanol; esters such as, for example, ethyl acetate or butyl acetate; or ketones such as, for example, acetone, methyl ethyl ketone or methyl isobutyl ketone. These solvents evaporate at room temperature and therefore do not remain within the wood. It is also possible, however, to add high-boiling liquids which remain in the wood, examples being higher alkanols, glycols, glycol ethers, glycol esters or polyglycols. The primer may also contain a binder, as conventional for wood coatings. This binder may comprise, for example, alkyd resins and modified alkyd resins, auto-crosslinking or externally crosslinking acrylate resins, polyester resins, drying oils, phenolic resins, nitrocellulose or mixtures thereof.

The basecoat may also contain one or more esters of phosphorous acid. Examples of such esters of phosphorous acid are: triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite. Tris(2,4-di-tert-butylphenyl) phosphite is particularly preferred.

The primer coat may also contain preservatives, for example fungicides or insecticides. Examples of fungicides which can be used are tributyltin oxide, phenylmercury salts, copper naphthenate, 1-chloronaphthalene or pentachlorophenol. Examples of insecticides which can be used are DDT, dieldrin, lindane, parathion or phoxim.

Further additives which may be present in the primer are curing accelerators (dryers) for the binders, dyes or else pigments, in small quantities.

The primer can be applied to the wood by the methods which are conventional for this purpose, for example by dipping, brushing or spraying.

The primer may also be an aqueous coating material. In this case, instead of the organic solvent, the vehicle comprises water or mixtures of water and a water-soluble organic solvent. The constituents may be in solution or dispersion in this vehicle.

The topcoat used may be any coating material which is suitable for the coating of wood. It usually contains a binder in solution or dispersion in an organic solvent or in water or in a water/solvent mixture. The binder may be, for example, an air-drying coating resin or a coating resin which is curable at room temperature. Examples of these resins are nitrocellulose, polyvinyl acetate, polyvinyl chloride, unsaturated polyester resins, polyacrylates, polyurethanes, epoxy resins, phenolic resins, but especially alkyd resins. The binder may also be a mixture of different coating resins. To the extent that the binders are curable, they are usually employed together with a curing agent and/or a curing accelerator. The systems involved may be 1-component or multicomponent systems.

The organic solvents used may be solvents which are conventional for coating materials, examples being aliphatic, aromatic or cycloaliphatic hydrocarbons, alcohols, esters, ketones or chlorinated hydrocarbons.

Examples of water/solvent mixtures are mixtures of water with lower alcohols, glycols or glycol ethers.

The topcoat may also be a composition of photopolymerizable compounds which is curable by actinic radiation. Examples of these are mixtures of acrylates and/or methacrylates, unsaturated polyester/styrene mixtures or mixtures of other ethylenically unsaturated monomers and/or oligomers.

The topcoat may contain a soluble dye and/or a pigment and/or a filler. The pigment may be an organic, inorganic or metallic pigment. The filler may be, for example, talc, kaolin, calcium carbonate or aluminum silicate. The topcoat is preferably a clearcoat; in other words, it contains no undissolved constituents.

The topcoat consists principally of a solvent and contains, for example, from 0.1 to 30% by weight, preferably from 0.1 to 5% by weight, of the benzophenone of the formula (I), based in each case on the solids content of the coating material.

In addition to the benzophenone of the formula (I) it is also possible to add further light stabilizers, especially sterically hindered amines of the 2,2,6,6-tetraalkylpiperidine type, to the protective coating for wood, examples of these light stabilizers being:

2.1. 2-(2'-hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis($\alpha,\alpha$-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-ylphenol]; transesterification product of 2-[3'-tert-butyl-5'-(2-methoxycarbonylethyl)-2'-hydroxyphenyl]benzotriazole with polyethylene glycol 300; [R—CH$_2$CH$_2$—COO (CH$_2$)$_3$ ]$_2$— where R=3'-tert-butyl-4'-hydroxy-5'-2H-benzotriazol-2-ylphenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy, and 2'-hydroxy-4,4'-dimethoxy derivative.

2.3. Esters of substituted or unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate and 2-methyl-4,6-di-tert-butylphenyl 3,5-di-tert-butyl-4-hydroxybenzoate.

2.4. Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 complex or the 1:2 complex, if appropriate with additional ligands such as n-butylamine, triethanolamine or N-cyclohexyldiethanolamine, nickel dibutyldithiocarbamate, nickel salts of monoalkyl 4-hydroxy-3,5-di-tert-butylbenzylphosphonates, such as of the methyl or ethyl ester, nickel complexes of ketoximes, such as of 2-hydroxy-4-methylphenyl undecyl ketoxime, and nickel complexes of 1-phenyl-4-lauroyl-5-hydroxypyrazole, if appropriate with additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, condensation product of 1-hydroxyethyl-2,2,6,6- tetramethyl-4-hydroxypiperidine and succinic acid, condensation product of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl)-1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4,5]decane-2,4-dione, bis(1-octyloxy-2,2,6,6-tetramethylpiperidyl) sebacate, bis(1-octyloxy-2,2,6,6-tetramethylpiperidyl) succinate, condensation product of N,N'-bis(2,2,6,6-tetramethyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4,5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine-2,5-dione.

2.7. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and the mixture thereof with 2-ethoxy-2'-ethyl-5,4'-di-tert-butyloxanilide, mixtures of o- and p-methoxy- and of o- and p-ethoxy-di-substituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyl-oxypropyloxy)phenyl]-4,6-bis(2,4-dimethylphenyl)-1,3,5-triazine and 2-[2-hydroxy-4-(2-hydroxy-3-octyloxypropyloxy)phenyl]-4,6-bis(2,4-dimethylphenyl)-1,3,5-triazine.

Preferred light stabilizers in this context are those of classes 2.1, 2.2, 2.6 and 2.8.

It is particularly effective to add a mixture of a UV absorber, for example a compound of the above classes 2.1, 2.2, 2.3, 2.4, 2.7 and 2.8, preferably 2.1 and 2.8, with a sterically hindered amine, for example a compound of the above class 2.6.

It is also possible to add antioxidants to the protective coating for wood, examples of these antioxidants being:

1.1. alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methyl-undec-1'-yl)phenol, 2,4-dimethyl-6-(1'-methyl-heptadec-1'-yl)phenol, 2,4-di-methyl-6-(1'-methyl-tridec-1'-yl)phenol and mixtures thereof.

1.2. Alkylthiomethylphenols, for example 2,4-di-octylthiomethyl-6-tert-butylphenol, 2,4-di-octylthiomethyl-6-methylphenol, 2,4-di-octylthiomethyl-6-ethylphenol and 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec.-amylphenol), 4,4'-bis(2,6-dimethyl-4-hydroxyphenyl) disulfide. 1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis (4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis (5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4- hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane and 1,1,5,5-tetra(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl 4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide and isooctyl 3,5-di-tert-butyl-4-hydroxybenzylmercaptoacetate.

1.8. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl)malonate, di-dodecylmercaptoethyl 2,2-bis(3,5-di-tert-butyl-4-hydroxybenzyl)malonate, and di- [4-(1,1,3,3-tetramethylbutyl)phenyl] 2,2-bis(3,5-di-tert-butyl-4-hydroxybenzyl)malonate.

1.9. Hydroxybenzyl aromatic compounds, for example 1,3,5-tris (3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene and 2,4,6-tris (3,5-di-tert-butyl-4-hydroxybenzyl)phenol.

1.10. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl) isocyanurate.

1.11. Benzyl phosphonates, for example dimethyl-2,5-di-tert-butyl-4-hydroxybenzylphosphonate, diethyl- 3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate and the calcium salt of 3,5-di-tert-butyl-4-hydroxybenzylphosphonic acid monoethyl ester.

1.12. Acylaminophenols, for example 4-hydroxylauranilide, 4-hydroxystearanilide and octyl N-(3,5-di-tert-butyl-4-hydroxyphenyl)carbamate.

1.13. Esters of β-(3,5-di-tert-butyl-4-hydroxyphenyl) propionic acid with monohydric or polyhydric alcohols, for example with methanol, ethanol, octanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris (hydroxyethyl) isocyanurate, N,N'-bis(hydroxyethyl) oxalamide, 3-thiaundecanol, 3-thiapentadecanol, trimethylhexanediol, trimethylolpropane and 4-hydroxymethyl-1-phospha-2,6,7-trioxabicyclo[2.2.2] octane.

1.14. Esters of β-(5-tert-butyl-4-hydroxy-3-methylphenyl)propionic acid with monohydric or polyhydric alcohols, for example with methanol, ethanol, octanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl) isocyanurate, N,N'-bis(hydroxyethyl) oxalamide, 3-thiaundecanol, 3-thiapentadecanol, trimethylhexanediol, trimethylolpropane and 4-hydroxymethyl-1-phospha-2,6,7-trioxabicyclo[2.2.2] octane.

1.15. Esters of β-(3,5-dicyclohexyl-4-hydroxyphenyl) propionic acid with monohydric or polyhydric alcohols, for example with methanol, ethanol, octanol, octadecanol, 1,6-hexanediol, 1,9-nonanediol, ethylene glycol, 1,2-propanediol, neopentylglycol, thiodiethylene glycol, diethylene glycol triethylene glycol, pentaerythritol, tris (hydroxyethyl) isocyanurate, N,N'-bis(hydroxyethyl) oxalamide, 3-thiaundecanol, 3-thiapentadecanol, trimethylhexanediol, trimethylolpropane and 4-hydroxymethyl-1-phospha-2,6,7-trioxabicyclo[2.2.2] octane.

1.16. Esters of 3,5-di-tert-butyl-4-hydroxyphenylacetic acid with monohydric or polyhydric alcohols, for example with methanol, ethanol, octanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris (hydroxyethyl) isocyanurate, N,N'-bis(hydroxyethyl) oxalamide, 3-thiaundecanol, 3-thiapentadecanol, trimethylhexanediol, trimethylolpropane and 4-hydroxymethyl-1-phospha-2,6,7-trioxabicyclo[2.2.2] octane.

1.17. Amides of 1-(3,5-di-tert-butyl-4-hydroxyphenyl) propionic acid, for example N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine and N,N'-bis(3,5-di-tert-butyl-4-hydroxyphenylpropionyl)hydrazine.

The topcoat may also contain additives which are conventional in paint technology, for example levelling assistants, thioxotropic agents, flameproofing agents, antioxidants or soluble dyes.

The protective coatings for wood are applied by the conventional methods for coating wood, for example by spraying, spreading, brushing, pouring or dipping.

The topcoat can be applied in two or more coats in order to attain an adequate coat thickness. The thickness of the topcoat depends on the intended application.

The present invention relates furthermore to a benzophenone of the formula I

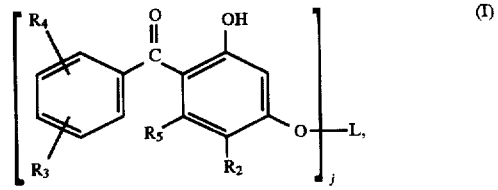

in which i is a number from one to four;

L if i is one is H, $C_1$-$C_{20}$alkyl, $C_2$-$C_{20}$alkyl which is substituted by one or two —OH, by carboxyl, by $C_1$-$C_{12}$alkoxy, by phenoxy, by $C_2$-$C_{20}$allkylcarbonyl, by $C_3$-$C_{20}$alkenylcarbonyl, by $C_2$-$C_{20}$alkanoyloxy, by $C_3$-$C_{20}$alkenoyloxy or by phenyl, glycidyl, $C_4$-$C_{20}$alkyl which is interrupted by one to six O atoms or by one or two carbonyloxy or oxycarbonyl groups, $C_2$-$C_{18}$alkenyl, $C_2$-$C_{18}$alkanoyl, $C_3$-$C_{18}$alkenoyl, benzoyl, benzoyl which is substituted by one or two $C_1$-$C_4$alkyl groups, substituted or unsubstituted phenyl or naphthyl, or a group of the formula II, III, IV, V or VI:

—$(CH_2)_j$—CH(OH)—$(CH_2)_k$—O—$R_9$  (II) where j, k=0–4;

—$(CH_2)_m$—$COOR_9$ (III) where m=1–4;
in which $R_9$ is $C_1$-$C_{18}$alkyl or phenyl;

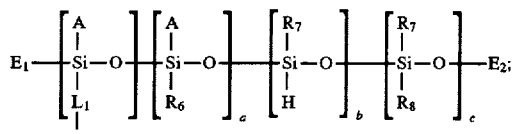
(IV)

in which
a=0–50, b=0–50 and c=0–50;
A is $R_7$ or —$O$—$Si(R_7)_3$;
$E_1$ is OH, $C_1$-$C_{12}$alkyl, $C_1$-$C_4$alkoxy, cyclohexyl, phenyl or —$O$—$Si(R_7)_3$;
$E_2$ is H, $C_1$-$C_{12}$alkyl, cyclohexyl, phenyl, —$Si(R_7)_3$ or —$Si(R_6)(R_7)_2$;
in which $E_1$ and $E_2$ together may also be a direct bond;
$L_1$ is a direct bond or a divalent group of the formula
—$C_nH_{2n}$—, —$(CH_2)_n$—$O$—,
—$CH_2CH(OH)CH_2$—$O$— or —$CH_2CH(OH)CH_2$—$O$—$(CH_2)_3$—, where n=1–4;
$R_6$ is a radical of the formula

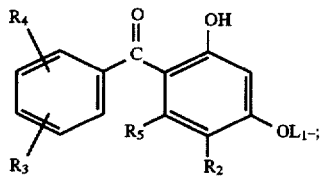

$R_7$ is $C_1$-$C_{12}$alkyl, $C_1$-$C_4$alkoxy, cyclohexyl or phenyl; and
$R_8$ is $C_1$-$C_{18}$alkyl, $C_1$-$C_4$alkoxy, $C_5$-$C_7$cycloalkyl or phenyl;

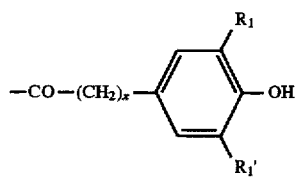
(V)

in which
x is 0, 1 or 2;
$R_1$ is $C_1$-$C_{12}$alkyl or $C_5$-$C_8$cycloalkyl; and
$R_1'$ is secondary or tertiary $C_3$-$C_{12}$alkyl or $C_5$-$C_8$cycloalkyl;

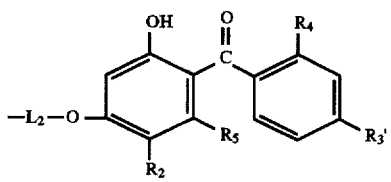
(VI)

in which $L_2$ is as defined for L if i is two; and
$R_3'$ is H or $C_1$-$C_{18}$alkyl;
L if i is two is $C_1$-$C_{12}$alkylene, $C_3$-$C_{12}$alkylene which is substituted by —OH, by $C_1$-$C_8$alkoxy, by $C_2$-$C_{20}$alkoxycarbonyl, by $C_2$-$C_{20}$alkanoyloxy, by $C_3$-$C_{20}$alkenoyloxy or by a silyl group of the formula (IV), $C_4$-$C_{20}$alkylene which is interrupted by one to six O atoms or by one or two carbonyloxy or oxycarbonyl groups, o-xylylene, m-xylylene, p-xylylene, isophthaloyl, phthaloyl, terephthaloyl or $\alpha,\omega$-$C_4$-$C_{12}$alkanedioyl;

L if i is three is $C_3$-$C_{12}$alkanetriyl, $C_3$-$C_{12}$alkanetrioyl, trimellitoyl or $C_6$-$C_{20}$alkanetriyl which is interrupted by three carbonyloxy or oxycarbonyl groups;
L if i is four is $C_4$-$C_{16}$alkanetetrayl, $C_4$-$C_{16}$alkanetetroyl, pyromellitoyl or $C_8$-$C_{24}$alkanetetrayl which is interrupted by four carbonyloxy or oxycarbonyl groups;
$R_2$ is H, $C_1$-$C_{18}$alkyl or Cl;
$R_3$ is —$SOR_{10}$ or —$SO_2R_{10}$;
$R_4$ is H, —OH, $C_1$-$C_{18}$alkyl or $C_2$-$C_{18}$alkenyl;
$R_5$ is H, —OL, where L is as defined for if i is one, or Cl; and
$R_{10}$ is $C_1$-$C_{20}$alkyl, $C_2$-$C_{20}$alkyl which is substituted by —OH, by $C_1$-$C_{12}$alkoxy, by a silyl group of the formula (IV), by $C_2$-$C_{12}$alkanoyloxy, by $C_3$-$C_{12}$alkenoyloxy or by halogen, $C_3$-$C_{18}$aLlcenyl, $C_5$-$C_{12}$cycloalkyl, $C_7$-$C_{15}$phenylalkyl, $C_6$-$C_{10}$aryl, $C_6$-$C_{10}$aryl which is substituted by one or two $C_1$-$C_4$alkyl groups, or 1,1,2,2-tetrahydroperfluoro-$C_6$-$C_{16}$alkyl.

The compounds according to the invention, to which the preferences specified above apply analogously, can be prepared by conventional methods of organic chemistry from the compounds which are already known from the prior art.

The examples which follow indicate possible implementations of the invention in detail. In these examples parts and percentages are by weight.

EXAMPLE 1

2-Hydroxy-4-dodecyloxy-4'-chlorobenzophenone

A mixture of 20 g (80 mmol) of 2,4-dihydroxy-4'-chlorobenzophenone, 21.9 g (88 mmol) of 1-bromododecane and 8.4 g (100 mmol) of sodium hydrogen carbonate in 77.6 g of sec-butyl alcohol and 25.6 g of $H_2O$ is heated with stirring and maintained at reflux for 20 h. The reaction mixture is stirred for an additional 15 min in the presence of 0.8 g of activated charcoal and is then filtered while hot. After the filtrate has cooled, the product crystallizes. It is recrystallized from sec-butyl alcohol to give 21.5 g of pale yellow crystals having a melting point of 61°–63° C.

| Analysis | Calc.: | C 72.01 | H 7.93 | Cl 8.50 |
|---|---|---|---|---|
| ($C_{25}H_{33}ClO_3$) | Found: | C 72.07 | H 8.14 | Cl 8.52 |

EXAMPLE 2

2-Hydroxy-4-[3-tris(trimethylsiloxy)silyl]propyloxy-4'-chlorobenzophenone

A mixture of 20 g (80 mmol) of 2,4-dihydroxy-4'-chlorobenzophenone, 59.7 g (160 mmol) of 3-chloropropyltris(trimethylsiloxy)silane, 1.33 g of potassium iodide and 13.2 g of potassium carbonate in 200 ml of N,N-dimethylacetamide is stirred under $N_2$ at 85° C. for 3 h. The reaction mixture is cooled and then concentrated in vacuo. The oily residue is purified by chromatography (ethyl acetate/hexane 1:100). 17.5 g of the compound are obtained as a pale yellow oil.

| Analysis | Calc.: | C 51.29 | H 7.06 | Cl 6.06 |
|---|---|---|---|---|
| ($C_{25}H_{41}ClO_6Si_4$) | Found: | C 50.80 | H 7.33 | Cl 6.60 |

EXAMPLE 3

2-Hydroxy-4-[3-tris(trimethylsiloxy)silyl]propyloxy-5-(1,1,3,3-tetramethylbutyl)benzophenone Example 2 is repeated but using as starting product 2,4-dihydroxy-5-(1,1,3,3-tetramethylbutyl)benzophenone.

The compound is obtained as a pale yellow oil.

| Analysis | Calc.: | C 59.77 | H 8.82 |
|---|---|---|---|
| ($C_{33}H_{58}O_6Si_4$) | Found: | C 59.41 | H 8.67 |

EXAMPLE 4

2-Hydroxy-4-dodecyloxy-5-chlorobenzophenone

Example 1 is repeated but using as starting product 2,4-dihydroxy-5-chlorobenzophenone. The compound is obtained as pale yellow crystals having a melting point of 75°–77° C.

| Analysis | Calc.: | C 72.01 | H 7.98 | Cl 8.50 |
|---|---|---|---|---|
| ($C_{25}H_{33}ClO_3$) | Found: | C 72.03 | H 8.04 | Cl 8.24 |

EXAMPLE 5

2-Hydroxy-4-methoxy-6-chlorobenzophenone 14.1 g (100 mmol) of benzoyl chloride are added dropwise with stirring at room temperature to a solution of 19 g (10 mmol) of 1-chloro-3,5-dimethoxybenzene and 14.7 (110 mmol) of $AlCl_3$ in 100 ml of toluene. The mixture is held at 70° C. with stirri for 5 h. The reaction mixture is cooled, then treated with 10% HCl and extracted with toluene. The resulting solution is washed with water and subsequently with saturated sodium chloride solution. The residue which remains after drying over $MgSO_4$, filtering and concentrating by evaporation is purified by chromatography over silica gel (ethyl acetate/hexane 1:5). The product is recrystallized from hexane. 13.9 g of the compound are obtained as pale yellow crystals having a melting point of 92°–94° C.

| Analysis | Calc.: | C 64.01 | H 4.22 | Cl 13.50 |
|---|---|---|---|---|
| ($C_{14}H_{11}ClO_3$) | Found: | C 63.90 | H 4.20 | Cl 13.56 |

EXAMPLE 6

2-Hydroxy-4,6-didodecyloxybenzophenone

A mixture of 4.5 g (20 mmol) of 2,4,6-trihydroxybenzophenone, 9.8 g (40 mmol) of 1-bromododecane, 2.7 g (20 mmol) of potassium carbonate and 30 mg (0.2 mmol) of potassium iodide in 50 ml of toluene and 20 ml of N,N-dimethylacetamide is stirred at 110° C. for 7 h. The reaction mixture is cooled and then neutralized with 10% HCL The organic solution is washed with water and then with saturated sodium chloride solution. The residue which remains after drying over $MgSO_4$, filtering and concentrating by evaporation is purified by chromatography over silica gel (toluene/hexane 3:2). The product is recrystallized from isopropyl alcohol. 4.1 g of the compound are obtained as pale yellow crystals having a melting point of 37°–38° C.

| Analysis | Calc.: | C 78.40 | H 10.31 |
|---|---|---|---|
| ($C_{37}H_{58}O_4$) | Found: | C 78.37 | H 10.27 |

EXAMPLE 7

2-Hydroxy-4'-phenylthio-4-dodecyloxybenzophenone

A mixture of 77.1 g(0.31 mol) of 2,4-dihydroxy-4'-chlorobenzophenone, 44.4 g (0.4 mol) of thiophenol and 51.4 g (0.37 mol) of potassium carbonate in 600 ml of 2-methyl-2-pyrrolidone is heated with stirring and he ld at 150° C. for 7 h. The reaction mixture is cooled, then treated with 125 ml of 10% HCl and extracted with ethyl acetate. The resulting solution is washed with water and then with saturated sodium chloride solution. The residue which remains after drying over $MgSO_4$, filtering and concentrating by evaporation is recrystallized from $CH_2Cl_2$/hexane . 52.6 g (52.6%) of 2,4-dihydroxy-4'-phenylthiobenzophenone are obtained as beige crystals having a melting point of 114°–116° C.

A mixture of 7.7 g (24 mmol) of 2,4-dihydroxy-4'-phenylthiobenzophenone, 6.6 g (26.4 mmol) of 1-bromododecane, 3.3 g (24 mmol) of potassium carbonate and 40 mg (0.024 mmol) of potassium iodide in 100 ml of xylene and 50 ml of N,N-dimethylacetamide is stirred at 130° C. for 3 h. The reaction mixture is cooled, then treated with 100 ml of water and extracted with ethyl acetate. The resulting solution is washed with water and then with saturated sodium chloride solution. The residue which remains after drying over $MgSO_4$, filtering and concentrating by evaporation is recrystallized from isopropanol. 10.5 g (89%) of the compound are obtained as pale yellow crystals having a melting point of 59°–60° C.

| Analysis | Calc.: | C 75.88 | H 7.81 | S 6.53 |
|---|---|---|---|---|
| ($C_{31}H_{38}O_3S$) | Found: | C 75.90 | H 7.81 | S 6.68 |

EXAMPLE 8

2-Hydroxy-4-(1,3-dimethylbutyloxy)-5-(1,1-dimethylpropyl)benzophenone 42 g (0.6 mol) of 2-methyl-2-butene are added dropwise to a solution of 45 g (0.21 mol) of 2,4-dihydroxybenzophenone and 6.1 g (63 mmol) of methanesulfonic acid in 90 ml of toluene and the mixture is held at 75° C. with stirring for 6 h. The reaction mixture is cooled, then treated with 100 ml of $NaHCO_3$ and extracted with ethyl acetate. The resulting solution is washed with water and then with saturated sodium chloride solution. The residue which remains after drying over $MgSO_4$, filtering and concentrating by evaporation is recrystallized from $CH_2Cl_2$/hexane. 53.6 g (89.9%) of 2,4-dihydroxy-5-(1,1-dimethylpropyl)benzophenone are obtained as beige crystals having a melting point of 100°–104° C.

A mixture of 10 g (35 mmol) of 2,4-dihydroxy-5-(1,1-dimethylpropyl)benzophenone, 11 g (66 mmol) of 2-bromo-4-methylpentane and 9.7 g (70 mmol) of potassium carbonate in 50 ml of xylene and 20 ml of N,N-dimethylacetamide is heated with stirring and held at 125° C. for 6 h. The reaction mixture is cooled, then treated with 30 ml of water and extracted with ethyl acetate. The resulting solution is washed with water and then with saturated sodium chloride solution. The residue which remains after drying over $MgSO_4$, filtering and concentrating by evaporation is distilled in a bulb tube (200° C./0. 1 mbar). 11.2 g (86.4%) of the compound are obtained as a yellow liquid.

| Analysis | Calc.: | C 78.22 | H 8.75 |
|---|---|---|---|
| ($C_{24}H_{32}O_3$) | Found: | C 78.17 | H 8.86 |

EXAMPLE 9

Mixture of 2-hydroxy-4-(2-hydroxy-1-phenylethyloxy- and -2-phenylethyloxy)-5-(1,1-dimethylpropyl)benzophenone A mixture of 10 g (35 mmol) of 2,4-dihydroxy-5-(1,1-dimethylpropyl)benzophenone, 4.65 g (38 mmol) of phenylethylene oxide and 1.3 g (3.5 mmol) of ethyltriphenylphosphonium bromide in 30 ml of xylene is stirred at 135° C. for 3 h. The reaction mixture is cooled and then filtered over Prolith rapid bleaching earth. The residue which remains after concentrating by evaporation is distilled in a bulb tube (250° C./0.1 mbar). 5.3 g (37%) of the compound are obtained as a yellow liquid.

| Analysis | Calc.: | C 77.20 | H 6.98 |
|---|---|---|---|
| ($C_{26}H_{28}O_4$) | Found: | C 77.20 | H 7.20 |

EXAMPLE 10

2-Hydroxy-4-(2-hydroxy-3-phenoxypropyloxy)-5-(1,1-dimethylpropyl)benzophenone

A mixture of 10 g (35 mmol) of 2,4-dihydroxy-5-(1,1-dimethylpropyl)benzophenone, 5.8 g (38 mmol) of phenyl glycidyl ether, 1.3 g (3.5 mmol) of ethyltriphenylphosphonium bromide in 30 ml of xylene is stirred at 135° C. for 3 h. The reaction mixture is cooled and then filtered over Prolith rapid bleaching earth. The residue which remains after concentrating by evaporation is distilled in a bulb tube (250° C./0.1 mbar). 10.5 g (69%) of the compound are obtained as a viscous yellow liquid.

| Analysis | Calc.: | C 74.63 | H 6.96 |
|---|---|---|---|
| ($C_{27}H_{30}O_5$) | Found: | C 74.73 | H 7.04 |

EXAMPLE 11

2-Hydroxy-4-isooctyl-5-(1,1-dimethylpropyl)benzophenone

A mixture of 10 g (35 mmol) of 2,4-dihydroxy-5-(1,1-dimethylpropyl)benzophenone, 7.9 g (38 mmol) of isobromooctane (mixture of isomers), 9.7 g (70 mmol) of potassium carbonate and 0.6 g (3.5 mmol) of potassium iodide in 30 ml of xylene is stirred at 110° C. for 8 h. The reaction mixture is cooled, then treated with 100 ml of water and extracted with ethyl acetate. The resulting solution is washed with water and then with saturated sodium chloride solution. The residue which remains after drying over $MgSO_4$, filtering and concentrating by evaporation is distilled in a bulb tube (190° C./4 mbar). 11.2 g (86.4%) of the compound are obtained as a yellow liquid.

| Analysis | Calc.: | C 78.75 | H 9.15 |
|---|---|---|---|
| ($C_{26}H_{36}O_3$) | Found: | C 78.72 | H 9.36 |

EXAMPLE 12

The compounds according to the invention (the percentages in Tables 1–4 relate to the solids content of the clearcoat) are dissolved initially in about 5 g of xylene and are incorporated into a clearcoat having the following composition:

| | |
|---|---|
| Jägalyd Antihydro ® (60% in white spirit)[1] | 53.48 |
| Jägalyd Antihydro Thix ® (50% in white spirit(Solv.)[2] | 10.69 |
| Jägalyd Antihydro Trockner ®[3] | 1.92 |
| White spirit | 33.27 |
| Ascinin P ®[4] | 0.32 |
| Luactim M ®[5] | 0.32 |
| | 100.0 |

The clearcoat is applied (three times by brush, with drying at room temperature for 24 h between each application) to a wood substrate (spruce) coated with an impregnating varnish (see below). After storage for 2 weeks at room temperature the samples are weathered in a Xenon-Weatherometer® (from Atlas Corp.) (cycle 7; 102:18 [ratio of dry to wet phase in minutes]). The 60° gloss is determined in accordance with DIN 67530; the yellowness index (YI) is determined in accordance with ASTM D 1925-88.

| Impregnating glaze | |
|---|---|
| Jägalyd Antihydro ® (60% in white spirit)[1] | 27.00 |
| Jägalyd Antihydro Trockner ®[3] | 1.00 |
| Ethylglycol | 3.00 |
| Traetex 293 ®[6] | 1.30 |
| Luactim M ®[5] | 0.20 |
| White spirit | 52.50 |
| Xylene | 15.00 |
| | 100.0 |

Application of the impregnating glaze: once by brush, then storage at room temperature for 24 h before the clearcoat is applied.

1) Alkyd resin from Ernst Jager GmbH & Co; DE
2) Thixotropic agent from Ernst Jager GmbH & Co; DE
3) Curing catalyst from Ernst Jager GmbH & Co; DE
4) Antiskinning agent from Bayer AG; DE
5) Antiskinning agent from BASF AG; DE
6) Fungicide from Acima AG; CH

TABLE 1

| Increase in YI after weathering for 801 hours | |
|---|---|
| a) unstabilized | 26.7 |
| b) 2% of the compound of Ex. 1 | 8.7 |
| c) 2% of the compound of Ex. 2 | 14.1 |
| d) 2% of the compound of Ex. 3 | 6.9 |
| e) 2% of the compound of Ex. 7 | 5.6 |

TABLE 2

| Gloss after weathering for 0, 1239 and 1405 hours | | | |
|---|---|---|---|
| | 0 | 1239 | 1405 |
| a) unstabilized | 94 | 70 | 53 |
| b) 2% of the compound of Ex. 4 | 95 | 84 | 76 |
| c) 2% of the compound of Ex. 6 | 92 | 76 | 67 |

In the case of b) and c) the coating material additionally contains 1% of bis (1-octyloxy-2,2,6,6-tetramethylpiperidyl) sebacate.

TABLE 3

| Increase in YI after weathering for 854 hours | |
|---|---|
| a) unstabalized | 28.1 |
| b) 2% of the compound of Ex. 8 | 14.5 |

TABLE 3-continued

| Increase in YI after weathering for 854 hours | |
|---|---|
| c) 2% of the compound of Ex. 9 | 18.1 |
| d) 2% of the compound of Ex. 10 | 19.2 |

In the case of b), c) and d) the coating material additionally contains 1% of bis(1-octyloxy-2,2,6,6-tetramethylpiperidyl) sebacate.

TABLE 4

| Increase in YI after weathering for 658 hours | |
|---|---|
| a) unstabilized | 27.5 |
| b) 2% of the compound of Ex. 11 | 20.3 |
| c) 1% of the compound of Ex. 11 | 12.1 |

In the case of b) and c) the coating material additionally contains 1% of bis(1-octyloxy-2,2,6,6-tetramethylpiperidyl) sebacate and, in the case of c), an additional 1% of 2-hydroxy-4-octyloxybenzophenone.

The samples stabilized in accordance with the invention display a better freedom from cracks (higher gloss values) and a lesser degree of yellowing (smaller increase in the YI value) than the comparison samples.

What is claimed is:

1. A protective coating composition for wood, which comprises at least one benzophenone of the formula I

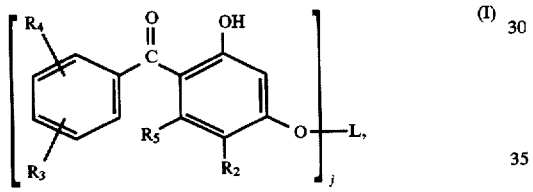

in which
i is a number from one to four,
L if i is one is H, $C_1$-$C_{20}$alkyl, $C_2$-$C_{20}$alkyl which is substituted by one or two —OH, by carboxyl, by $C_1$-$C_{12}$alkoxy, by phenoxy, by $C_2$-$C_{20}$alkylcarbonyl, by $C_3$-$C_{20}$alkenylcarbonyl, by $C_2$-$C_{20}$alkanoyloxy, by $C_3$-$C_{20}$alkenoyloxy or by phenyl, glycidyl, $C_4$-$C_{20}$alkyl which is interrupted by one to six O atoms or by one or two carbonyloxy or oxycarbonyl groups, $C_2$-$C_{18}$alkenyl, $C_2$-$C_{18}$alkanoyl, $C_3$-$C_{18}$alkenoyl, benzoyl, benzoyl which is substituted by one or two $C_1$-$C_4$alkyl groups, substituted or unsubstituted phenyl or naphthyl, or a group of the formula II, III, IV, V or VI:

—$(CH_2)_j$—CH(OH)—$(CH_2)_k$—O—$R_9$ (II) where j, k=0–4;

—$(CH_2)_m$—COOR$_9$ (III) where m=1–4;

in which $R_9$ is $C_1$-$C_{18}$alkyl or phenyl;

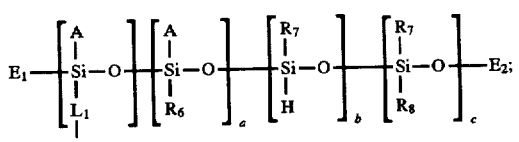

in which
a=0–50, b=0–50 and c=0–50;
A is $R_7$ or —O—Si($R_7$)$_3$;
$E_1$ is OH, $C_1$-$C_{12}$alkyl, $C_1$-$C_4$alkoxy, cyclohexyl, phenyl or —O—Si($R_7$)$_3$;
$E_2$ is H, $C_1$-$C_{12}$alkyl, cyclohexyl, phenyl, —Si($R_7$)$_3$ or —Si($R_6$)($R_7$)$_2$;

in which $E_1$ and $E_2$ together may also be a direct bond;
$L_1$ is a direct bond or a divalent group of the formula —$C_nH_{2n}$—, —$(CH_2)_n$—O—, —$CH_2CH(OH)CH_2$—O— or —$CH_2CH(OH)CH_2$—O—$(CH_2)_3$—, where n=1–4;
$R_6$ is a radical of the formula

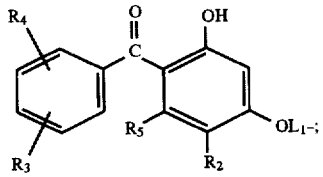

$R_7$ is $C_1$-$C_{12}$alkyl, $C_1$-$C_4$alkoxy, cyclohexyl or phenyl; and
$R_8$ is $C_1$-$C_{18}$alkyl, $C_1$-$C_4$alkoxy, $C_5$-$C_7$cycloalkyl or phenyl;

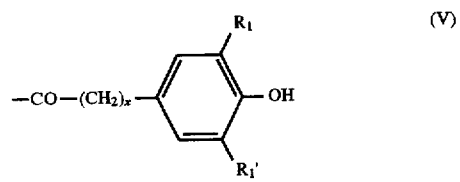

in which
x is 0, 1 or 2;
$R_1$ is $C_1$-$C_{12}$alkyl or $C_5$-$C_8$cycloalkyl; and
$R_1'$ is secondary or tertiary $C_3$-$C_{12}$alkyl or $C_5$-$C_8$cycloalkyl;

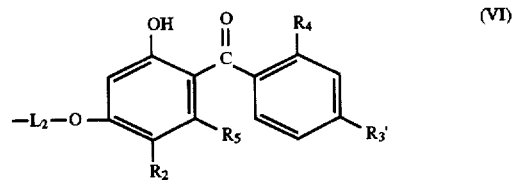

in which $L_2$ is as defined for L if i is two; and
$R_3'$ is H or $C_1$-$C_{18}$alkyl;
L if i is two is $C_1$-$C_{12}$alkylene, $C_3$-$C_{12}$alkylene which is substituted by —OH, by $C_1$-$C_8$alkoxy, by $C_2$-$C_{20}$alkoxycarbonyl, by $C_2$-$C_{20}$alkanoyloxy, by $C_3$-$C_{20}$alkenoyioxy or by a silyl group of the formula (IV), $C_4$-$C_{20}$alkylene which is interrupted by one to six O atoms or by one or twb carbonyloxy or oxycarbonyl groups, o-xylylene, m-xylylene, p-xylylene, isophthaloyl, phthaloyl, terephthaloyl or $\alpha,\omega$-$C_4$-$C_{12}$alkanedioyl;
L if i is three is $C_3$-$C_{12}$alkanetriyl, $C_3$-$C_{12}$alkanetrioyl, trimellitoyl or $C_6$-$C_{20}$alkanetriyl which is interrupted by three carbonyloxy or oxycarbonyl groups;
L if i is four is $C_4$-$C_{16}$alkanetetrayl, $C_4$-$C_{16}$alkanetetroyl, pyromellitoyl or $C_8$-$C_{24}$alkanetetrayl which is interrupted by four carbonyloxy or oxycarbonyl groups;
$R_2$ is H, $C_1$-$C_{18}$alkyl or Cl;
$R_3$ is H, Cl, —$SR_{10}$, —$SOR_{10}$ or —$SO_2R_{10}$;
$R_4$ is H, —OH, $C_1$-$C_{18}$alkyl or $C_2$-$C_{18}$alkenyl;
$R_5$ is H, —OL, where L is as defined for if i is one, or Cl; and
$R_{10}$ is $C_1$-$C_{20}$alkyl, $C_2$-$C_{20}$alkyl which is substituted by —OH, by $C_1$-$C_{12}$alkoxy, by a silyl group of the formula (IV), by $C_2$-$C_{12}$alkanoyloxy, by $C_3$-$C_{12}$alkenoyloxy, by halogen, $C_3$-$C_{18}$alkenyl, $C_5$-$C_{12}$cycloalkyl, $C_7$-$C_{15}$phenylalkyl, $C_6$-$C_{10}$aryl, $C_6$-$C_{10}$aryl which is substituted by one or two $C_1$-$C_4$alkyl groups, or 1,1,2,2-tetrahydroperfluoro-$C_6$-$C_{16}$alkyl;

under the condition that, if i is one, at least one of the radicals $R_2$, $R_3$ and $R_5$ is other than H.

2. A benzophenone of the formula I

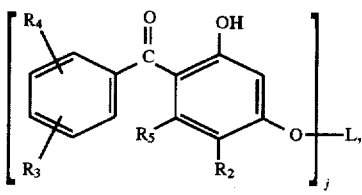

in which i is a number from one to four;

L if i is one is H, $C_1$-$C_{20}$alkyl, $C_2$-$C_{20}$alkyl which is substituted by one or two —OH, by carboxyl, by $C_1$-$C_{12}$alkoxy, by phenoxy, by $C_2$-$C_{20}$alkylcarbonyl, by $C_3$-$C_{20}$alkenylcarbonyl, by $C_2$-$C_{20}$alkanoyloxy, by $C_3$-$C_{20}$alkenoyloxy or by phenyl, glycidyl, $C_4$-$C_{20}$alkyl which is interrupted by one to six O atoms or by one or two carbonyloxy or oxycarbonyl groups, $C_2$-$C_{18}$alkenyl, $C_2$-$C_{18}$alkanoyl, $C_3$-$C_{18}$alkenoyl, benzoyl, benzoyl which is substituted by one or two $C_1$-$C_4$alkyl groups, substituted or unsubstituted phenyl or naphthyl, or a group of the formula II, III, IV, V or VI:

—$(CH_2)_j$—CH(OH)—$(CH_2)_k$—O—$R_9$ (II) where j, k=0–4;

—$(CH_2)_m$—COOR$_9$ (III) where m=1–4;

in which $R_9$ is $C_1$-$C_{18}$alkyl or phenyl;

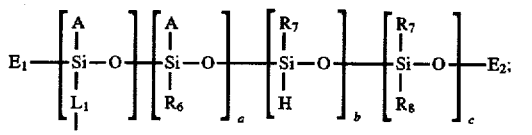

in which a=0–50, b=0–50 and c=0–50;

A is $R_7$ or —O—Si($R_7$)$_3$;

$E_1$ is OH, $C_1$-$C_{12}$alkyl, $C_1$-$C_4$alkoxy, cyclohexyl, phenyl or —O—Si($R_7$)$_3$;

$E_2$ is H, $C_1$-$C_{12}$alkyl, cyclohexyl, phenyl, —Si($R_7$)$_3$ or —Si($R_6$)($R_7$)$_2$;

in which $E_1$ and $E_2$ together may also be a direct bond;

$L_1$ is a direct bond or a divalent group of the formula —$C_nH_{2n}$—, —$(CH_2)_n$—O—, —$CH_2CH(OH)CH_2$—O— or —$CH_2CH(OH)CH_2$—O—$(CH_2)_3$—, where n=1–4;

$R_6$ is a radical of the formula

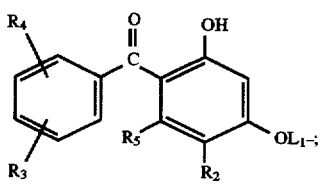

$R_7$ is $C_1$-$C_{12}$alkyl, $C_1$-$C_4$alkoxy, cyclohexyl or phenyl; and $R_8$ is $C_1$-$C_{18}$alkyl, $C_1$-$C_4$alkoxy, $C_5$-$C_7$cycloalkyl or phenyl;

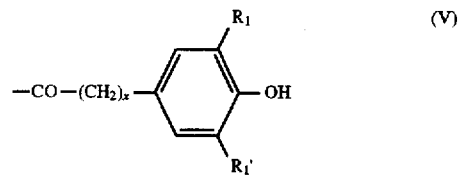

in which x is 0, 1 or 2;

$R_1$ is $C_1$-$C_{12}$alkyl or $C_5$-$C_8$cycloalkyl; and $R_1'$ is secondary or tertiary $C_3$-$C_{12}$alkyl or $C_5$-$C_8$cycloalkyl;

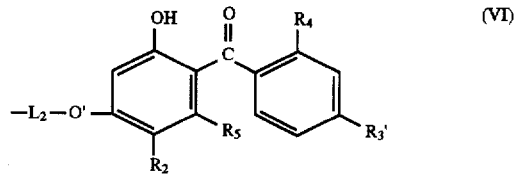

in which $L_2$ is as defined for L if i is two; and $R_3'$ is H or $C_1$-$C_{18}$alkyl;

L if i is two is $C_1$-$C_{12}$alkylene, $C_3$-$C_{12}$alkylene which is substituted by —OH, by $C_1$-$C_8$alkoxy, by $C_2$-$C_{20}$alkoxycarbonyl, by $C_2$-$C_{20}$alkanoyloxy, by $C_3$-$C_{20}$alkenoyloxy or by a silyl group of the formula (IV), $C_4$-$C_{20}$alkylene which is interrupted by one to six O atoms or by one or two carbonyloxy or oxycarbonyl groups, o-xylylene, m-xylylene, p-xylylene, isophthaloyl, phthaloyl, terephthaloyl or α,ω-$C_4$-$C_{12}$alkanedioyl;

L if i is three is $C_3$-$C_{12}$alkanetriyl, $C_3$-$C_{12}$alkanetrioyl, trimellitoyl or $C_6$-$C_{20}$alkanetriyl which is interrupted by three carbonyloxy or oxycarbonyl groups;

L if i is four is $C_4$-$C_{16}$alkanetetrayl, $C_4$-$C_{16}$alkanetetroyl, pyromellitoyl or $C_8$-$C_{24}$alkanetetrayl which is interrupted by four carbonyloxy or oxycarbonyl groups;

$R_2$ is H, $C_1$-$C_{18}$alkyl or Cl;

$R_3$ is —SOR$_{10}$ or —SO$_2$R$_{10}$;

$R_4$ is H, —OH, $C_1$-$C_{18}$alkyl or $C_2$-$C_{18}$alkenyl;

$R_5$ is H, —OL, where L is as defined for if i is one, or Cl; and $R_{10}$ is $C_1$-$C_{20}$alkyl, $C_2$-$C_{20}$alkyl which is substituted by —OH, by $C_1$-$C_{12}$alkoxy, by a silyl group of the formula (IV), by $C_2$-$C_{12}$alkanoyloxy, by $C_3$-$C_{12}$alkenoyloxy or by halogen, $C_3$-$C_{18}$alkenyl, $C_5$-$C_{12}$cycloalkyl, $C_7$-$C_{15}$phenylalkyl, $C_6$-$C_{10}$aryl, $C_6$-$C_{10}$aryl which is substituted by one or two $C_1$-$C_4$alkyl groups, or 1,1,2,2-tetrahydroperfluoro-$C_6$-$C_{16}$alkyl.

3. A method according to claim 1, wherein the benzophenone is of the formula I in which i is one;

L is H, $C_1$-$C_{12}$alkyl, $C_2$-$C_{12}$alkenyl, phenyl, naphthyl or a radical of the formula II, III or IV:

—$(CH_2)_j$—CH(OH)—$(CH_2)_k$—O—$R_9$ (II) where j, k=0–4;

—$(CH_2)_m$—COOR$_9$ (III) where m=1–4;

in which $R_9$ is $C_1$-$C_{18}$alkyl or phenyl;

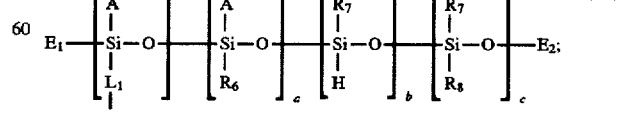

in which a=1–50, b=0 and c=0–50;

A is $R_7$ or —O—Si($R_7$)$_3$;

$E_1$ is OH, $C_1$-$C_{12}$alkyl, $C_1$-$C_4$alkoxy, cyclohexyl, phenyl or —O—Si($R_7$)$_3$;

$E_2$ is H, $C_1$-$C_{12}$alkyl, cyclohexyl, phenyl, —SiR6 ($R_7$)$_2$ or —Si($R_7$)$_3$;

in which $E_1$ and $E_2$ together may also be a direct bond;

$L_1$ is a direct bond or a divalent group of the formula —$C_nH_{2n}$—, —(CH$_2$)$_n$—O— or —CH$_2$CH(OH)CH$_2$—O—(CH$_2$)$_3$—, where n=1–4;

$R_6$ is a radical of the formula

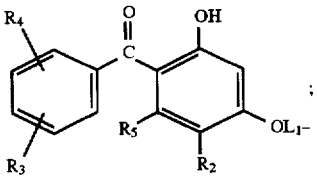

$R_7$ is $C_1$-$C_{12}$alkyl, $C_1$-$C_4$alkoxy, cyclohexyl or phenyl; and $R_8$ is $C_1$-$C_{18}$alkyl, $C_1$-$C_4$alkoxy, $C_5$-$C_7$cycloalkyl or phenyl;

$R_2$ is $C_1$-$C_{12}$alkyl or Cl or, if $R_5$ is —OL or Cl, is H;

$R_3$ is Cl, or, if $R_2$ or $R_5$ is other than H, is H;

$R_4$ is H, $C_1$-$C_{12}$alkyl or $C_2$-$C_{12}$alkenyl; and $R_5$ is H, —OL or Cl.

4. A method according to claim 1, wherein the benzophenone is of the formula I in which A)
i is one;
L is —CH$_2$—CH(OH)—CH$_2$—O—$R_9$ (II);
$R_2$ is $C_1$-$C_{12}$alkyl;
$R_3$, $R_4$ and $R_5$ are H; and
Rg is $C_1$-$C_{18}$alkyl; or B)
i is one;
L is $C_1$-$C_{12}$alkyl;
$R_2$ is $C_1$-$C_{12}$alkyl; and
$R_3$, $R_4$ and $R_5$ are H; or C)
i is one;
L is $C_1$-$C_{12}$alkyl;
$R_2$ is $C_1$-$C_{12}$alkyl;
$R_3$ is Cl; and
$R_4$ and $R_5$ are H; or D)
i is one;
L is —(CH)$_m$—COOR$_9$ (III) where m=1–4;
$R_2$ is $C_1$-$C_{12}$alkyl;
$R_3$, $R_4$ and $R_5$ are H; and
$R_9$ is $C_1$-$C_{18}$alkyl; or E)
i is one;
L is $C_1$-$C_{12}$alkyl;
$R_2$, $R_4$ and $R_5$ are H;
$R_3$ is —SR$_{10}$ or —SO$_2$R$_{10}$; and
$R_{10}$ is $C_1$-$C_{12}$alkyl or phenyl.

5. A method according to claim 2, wherein the benzophenone is of the formula I in which i is one;

L is H, $C_1$-$C_{12}$alkyl, $C_2$-$C_{12}$alkenyl, phenyl, naphthyl or a radical of the formula II, III or IV:

—(CH$_2$)$_j$—CH(OH)—(CH$_2$)$_k$—O—$R_9$ (II) where j, k=0–4;

—(CH$_2$)$_m$—COOR$_9$ (III) where m=1–4;

in which $R_9$ is $C_1$-$C_{18}$alkyl or phenyl;

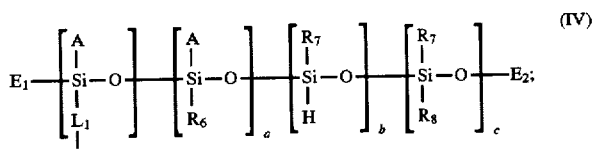

in which
a=1–50, b=0 and c=0–50;

A is $R_7$ or —O—Si($R_7$)$_3$;

$E_1$ is OH, $C_1$-$C_{12}$alkyl, $C_1$-$C_4$alkoxy, cyclohexyl, phenyl or —O—Si($R_7$)$_3$;

$E_2$ is H, $C_1$-$C_{12}$alkyl, cyclohexyl, phenyl, —SiR$_6$ ($R_7$)$_2$ or —Si($R_7$)$_3$;

in which $E_1$ and $E_2$ together may also be a direct bond;

$L_1$ is a direct bond or a divalent group of the formula —$C_nH_{2n}$—, —(CH$_2$)$_n$—O— or —CH$_2$CH(OH)CH$_2$—O—(CH$_2$)$_3$—, where n=1–4;

$R_6$ is a radical of the formula

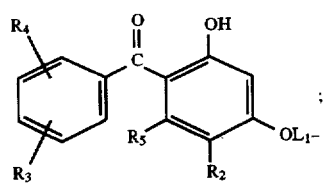

$R_7$ is $C_1$-$C_{12}$alkyl, $C_1$-$C_4$alkoxy, cyclohexyl or phenyl; and $R_8$ is $C_1$-$C_{18}$alkyl, $C_1$-$C_4$alkoxy, $C_5$-$C_7$cycloalkyl or phenyl;

$R_2$ is $C_1$-$C_{12}$alkyl or Cl or, if $R_5$ is —OL or Cl, is H;

$R_3$ is Cl, or, if $R_2$ or $R_5$ is other than H, is H;

$R_4$ is H, $C_1$-$C_{12}$alkyl or $C_2$-$C_{12}$alkenyl; and $R_5$ is H, —OL or Cl.

6. A method according to claim 2, wherein the benzophenone is of the formula I in which A)
i is one;
L is —CH$_2$—CH(OH)—CH$_2$—O—$R_9$ (II);
$R_2$ is $C_1$-$C_{12}$alkyl;
$R_3$, $R_4$ and $R_5$ are H; and
$R_9$ is $C_1$-$C_{18}$alkyl; or B)
i is one;
L is $C_1$-$C_{12}$alkyl;
$R_2$ is $C_1$-$C_{12}$alkyl; and
$R_3$, $R_4$ and $R_5$ are H; or C)
i is one;
L is $C_1$-$C_{12}$alkyl;
$R_2$ is $C_1$-$C_{12}$alkyl;
$R_3$ is Cl; and
$R_4$ and $R_5$ are H; or D)
i is one;
L is —(CH)$_m$—COOR$_9$ (III) where m=1–4;
$R_2$ is $C_1$-$C_{12}$alkyl;
$R_3$, $R_4$ and $R_5$ are H; and
$R_9$ is $C_1$-$C_{18}$alkyl; or E)
 i is one;
 L is $C_1$-$C_{12}$alkyl;
 $R_2$, $R_4$ and $R_5$ are H;
 $R_3$ is —$SR_{10}$ or —$SO_2R_{10}$; and
 $R_{10}$ is $C_1$-$C_{12}$alkyl or phenyl.

* * * * *